United States Patent
Wong et al.

(10) Patent No.: US 9,445,877 B2
(45) Date of Patent: Sep. 20, 2016

(54) ELECTRIC TOOTHBRUSH MODULE

(71) Applicant: J.T. Labs Limited, Fanling, Hong Kong SAR (CN)

(72) Inventors: Tit Shing Wong, Hong Kong (CN); Siu Wai Tang, Hong Kong (CN); Kwok Yau Cheung, Hong Kong (CN); Sui Kay Wong, Hong Kong (CN)

(73) Assignee: J.T. LABS LIMITED, Hong Kong SAR (CN)

( * ) Notice: Subject to any disclaimer, the term of this patent is extended or adjusted under 35 U.S.C. 154(b) by 53 days.

(21) Appl. No.: 14/481,656

(22) Filed: Sep. 9, 2014

(65) Prior Publication Data

US 2016/0067025 A1    Mar. 10, 2016

(51) Int. Cl.
*A61C 17/34* (2006.01)
*A61C 17/40* (2006.01)
*A61C 17/22* (2006.01)

(52) U.S. Cl.
CPC .............. *A61C 17/40* (2013.01); *A61C 17/222* (2013.01); *A61C 17/349* (2013.01); *A61C 17/3418* (2013.01); *A61C 17/3463* (2013.01); *A61C 17/3472* (2013.01)

(58) Field of Classification Search
CPC ...... A61C 17/22; A61C 17/32; A61C 17/34; A61C 17/3409; A61C 17/349; A61C 17/3418; A61C 17/3454; A46B 7/06; A46B 13/02
USPC .......................................................... 15/22.1
See application file for complete search history.

(56) References Cited

U.S. PATENT DOCUMENTS

| | | | |
|---|---|---|---|
| 5,778,474 A * | 7/1998 | Shek | A61C 17/349 15/22.1 |
| 5,794,295 A | 8/1998 | Shen | |
| 7,757,327 B2 * | 7/2010 | Filsouf | A61C 17/3472 15/22.1 |
| 2014/0310900 A1 | 10/2014 | Curry et al. | |
| 2015/0173872 A1 | 6/2015 | Dickie | |

FOREIGN PATENT DOCUMENTS

| | | | | |
|---|---|---|---|---|
| CN | 2294034 Y | 10/1998 | | |
| CN | 201223467 Y | 4/2009 | | |
| CN | 1596841 A | 3/2015 | | |
| CN | 204411009 U | 6/2015 | | |
| WO | WO 99/12492 | * | 3/1999 | A61C 17/34 |

* cited by examiner

*Primary Examiner* — Laura C Guidotti
(74) *Attorney, Agent, or Firm* — R. Neil Sudol; Henry D. Coleman

(57) ABSTRACT

A toothbrush has a frame, a bristle holder movably mounted to a distal end of the frame, and a power transmission assembly operatively connectable to a drive motor and operatively connected to the bristle holder so as to move bristle tips on the bristle holder along an oval path relative to the frame. In a single cycle of movement along the oval path, the bristles shift away from the frame and towards the teeth, then along and in contact with the teeth in a direction away from the gum line, then back towards the frame and away from the teeth, and subsequently along the frame and out of contact with the teeth.

14 Claims, 13 Drawing Sheets

ELECTRIC TOOTHBRUSH MODULE

BACKGROUND OF THE INVENTION

This invention relates to an electric toothbrush. The toothbrush may include a handle and an electric drive or, alternatively, may be a module that is attachable to a separate handle module that contains the drive.

One of the health problems experienced by an aging population is a receding of gums and a separation of the gums from the tooth surfaces. Members of this demographic are prone to cavities at or below the receding gum line. A reason for this shift in cavity incidence is the loosening or degeneration of the gums. Normal brushing of the teeth frequently results in the sweeping of food particles into the interstitial space between the gums and the teeth. These food particles inevitably support proliferating bacteria colonies and consequent tooth decay at or below the gum line.

OBJECTS OF THE INVENTION

It is an object of the present invention to provide an improved electric toothbrush.

It is a further object of the present invention to provide an electric toothbrush that brushes teeth in a way to reduce the incidence of tooth decay.

A more specific object of the present invention is to provide such a toothbrush that reduces the likelihood of food particles being swept under the gums.

Another object of the present invention is to provide such a toothbrush that automatically determines and induces an optimal mode of brush movement.

These and other objects of the present invention will be apparent from the descriptions and drawings herein. Although every object of the invention is attainable by at least one embodiment of the invention, there is not necessarily any single embodiment that achieves all of the objects of the invention.

SUMMARY OF THE INVENTION

A toothbrush module comprises, in accordance with the present invention, a frame assembly, a bristle holder movably mounted to a distal end of the frame assembly, and a power transmission assembly operatively connectable to a drive motor and operatively connected to the bristle holder so as to move bristle tips on the bristle holder along an oval path relative to the frame. In a single cycle of movement along the oval path, the bristles shift away from the frame and towards the teeth, then along and in contact with the teeth in a direction away from the gum line, then back towards the frame and away from the teeth, and subsequently along the frame and out of contact with the teeth.

The toothbrush frame may include a handle or a base that is connectable to a separate handle module. Typically, the drive motor is an electric motor housed in the handle portion of a complete toothbrush.

Preferably, the toothbrush module further comprises an orientation sensor mounted to the frame (handle or base) and adapted to detect an orientation of the frame. The orientation sensor is operatively connected to the drive motor and/or the power transmission assembly for controlling a direction of motion of the bristle holder so that the bristle tips trace the oval path in a direction depending on orientation of the frame.

The sensor is configured to detect at least two alternative orientations of the frame and to induce or enable a motion of the bristle holder in one direction when the toothbrush module is in a first of the alternative orientations and in an opposite direction when the toothbrush module is in a second of the alternative orientations. In brief, the orientation sensor functions to detect the direction that the bristles are facing, concomitantly, the side of the brush head on which the target tooth surface lies.

The sensor may take the form of a ball sensor. The ball completes a circuit including two of four contact pins provided in the toothbrush frame. Alternatively, the sensor includes a gravity switch or accelerometer.

Pursuant to another feature of the present invention, the power transmission assembly includes a camming element executing a motion that is eccentric relative to a power transmission axis. Typically, the power transmission axis is an axis of rotation of a motor rotor. The power transmission assembly further includes a camming-action receiver element formed with an aperture or opening, the camming element being disposed at least in part in the aperture in contact with a surface thereof. The receiver element also has a slot traversed by a pin stationary relative to the frame. The slot and pin allow a limited motion of the camming-action receiver element to generate the oval path of the brush bristles.

In one embodiment of the toothbrush module, the bristle holder includes the receiver element. The camming element and the camming-action receiver element are located in the brush head.

In an alternative embodiment of the toothbrush module, the camming element and the receiver element are disposed proximate a proximal end of the shaft or shank, for instance, inside a base portion of the frame which is connectable to a toothbrush handle or, alternatively, includes a toothbrush handle. The power transmission assembly includes a rod extending longitudinally through the shaft or shank. The rod is linked at a proximal end to the camming-action receiver element and at a distal end to the bristle holder. The rod is attached to a ball rotatably disposed in the shaft or shank between the handle and the brush head. The location of the ball determines in part the size of the oval path traced by the bristle tips.

Pursuant to a further feature of the present invention, the bristle holder is one of a plurality of bristle holders mutually interspaced along a brush head at a distal end of the frame. The bristle holders are spaced longitudinally along the axis of the frame. Each bristle holder is formed with a respective aperture or opening. The camming element is disposed partially inside each aperture so as to roll in contact with a surface of each aperture. The bristle holders may be fixed to one another, collectively serving as the camming-action receiver element. Alternatively, the bristle holders may be independent but execute a parallel motion in tandem, with the bristle tips all moving along the same oval path, owing to the common linkage to the camming element.

A toothbrush module comprises, in accordance with the present invention, (a) a base, (b) an elongate hollow shaft or shank connected to the base, the shaft or shank defining a longitudinal axis at a distal end, (c) a brush head mounted to the shaft or shank at an end thereof opposite the base, the brush head including a bristle holder movable relative to the shaft or shank and the base, and (d) a power transmission assembly operatively connected to a drive and to the bristle holder. The drive is typically an electric motor having a mechanical energy output element such as a rotor. The power transmission assembly is configured to convert a rotary motion of the rotor into a motion of the bristle holder such that bristle tips thereof trace a generally oval path relative to the shaft or shank and the handle. The oval path includes a first path segment towards a tooth surface, a second path segment along the tooth surface and away from a respective gum line, a third path segment away from the tooth surface, and a fourth path segment in a direction opposite the second path segment and spaced away from the tooth surface.

The toothbrush module may further comprising an orientation sensor as described hereinabove. In addition, the power transmission assembly may include a camming element and a camming-action receiver element as discussed above. The bristle holder may include the receiver element or, alternatively, the camming element and receiver element may be located in the base (which may or may not include a handle of the toothbrush) with the power transmission assembly including a rod extending longitudinally through the shaft or shank from the receiver element to the bristle holder.

Where the bristle holder is one of a plurality of bristle holders mutually interspaced along the brush head, each of the bristle holders being formed with a respective aperture, the camming element being disposed partially inside each aperture so as to roll in contact with a surface of each aperture, the apertures typically have a cross-section that is geometrically similar and larger than a cross-section of the camming element.

Pursuant to a feature of the present invention, the brush head includes at least one auxiliary bristle holder that is stationary with respect to the shaft or shank and the base.

The brush head may include a hollow housing disposed at an end of the shaft or shank opposite the base, the housing being stationary relative to the base, the bristle holder or holders being disposed partially inside the housing.

The present invention provides an electric toothbrush that brushes teeth in a way to reduce the incidence of tooth decay, by reducing the likelihood of food particles being swept under the gums. The invention contemplates a method of automatically brushing the teeth wherein ones operates a power transmission assembly, operatively connected to a bristle holder, so as to move bristle tips on the bristle holder along an oval path relative to a toothbrush frame. In a single cycle of movement along the oval path, the bristles shift away from the frame and towards the teeth, then along and in contact with the teeth in a direction away from the gum line, then back towards the frame and away from the teeth, and subsequently along the frame and out of contact with the teeth.

The method also contemplates an automatic control of the direction of movement of the bristle holder so that the bristle tips move in one direction or the opposite along the oval path, depending on brush orientation. The method may include operating a sensor to detect two alternative orientations of the frame and to induce or enable a motion of the bristle holder in one direction when the toothbrush is in a first of the alternative orientations and in an opposite direction when the toothbrush is in a second of the alternative orientations.

The operating of the power transmission assembly may include moving a camming element along a circuit that is eccentric relative to a power transmission axis and consequently moving a camming-action receiver element. The camming element and receiver element may have structures as described above.

DETAILED DESCRIPTION

Figure 1:
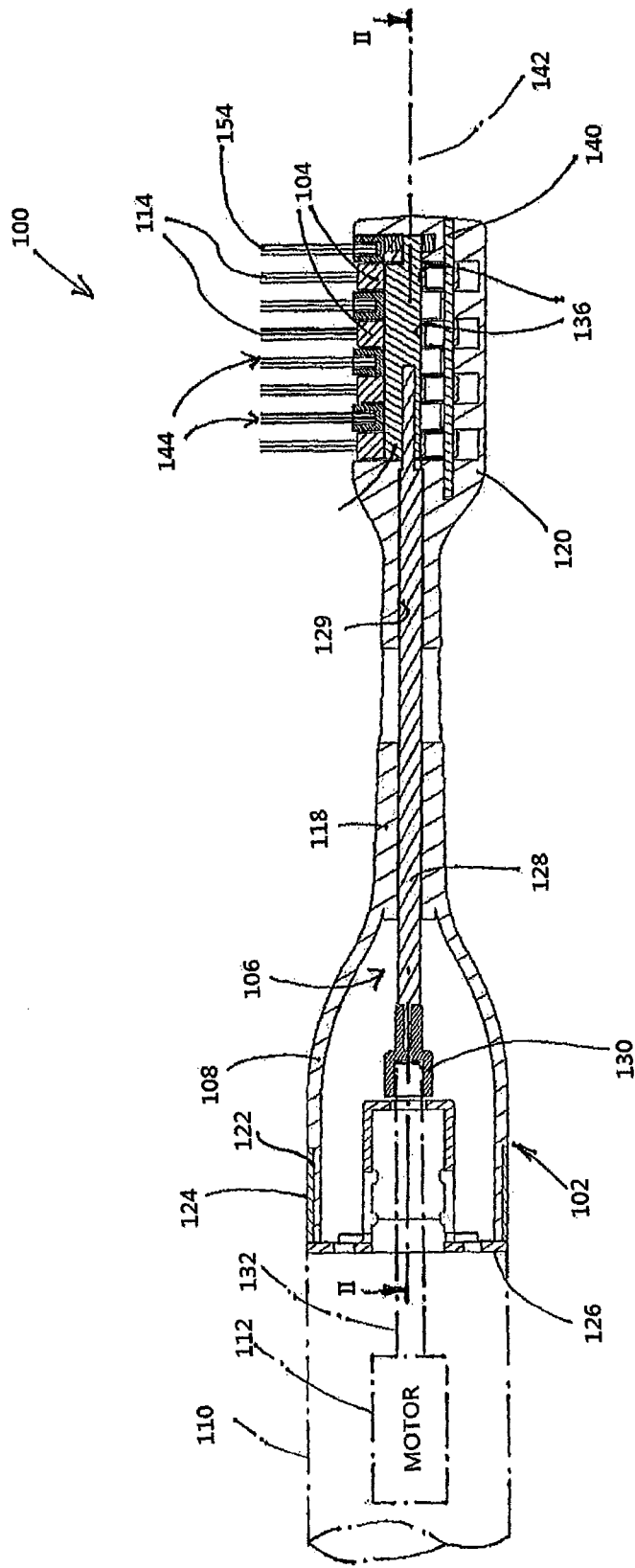
FIG. 1 is a longitudinal cross-sectional view of an electric toothbrush module or assembly in accordance with the present invention.
Figure 2:
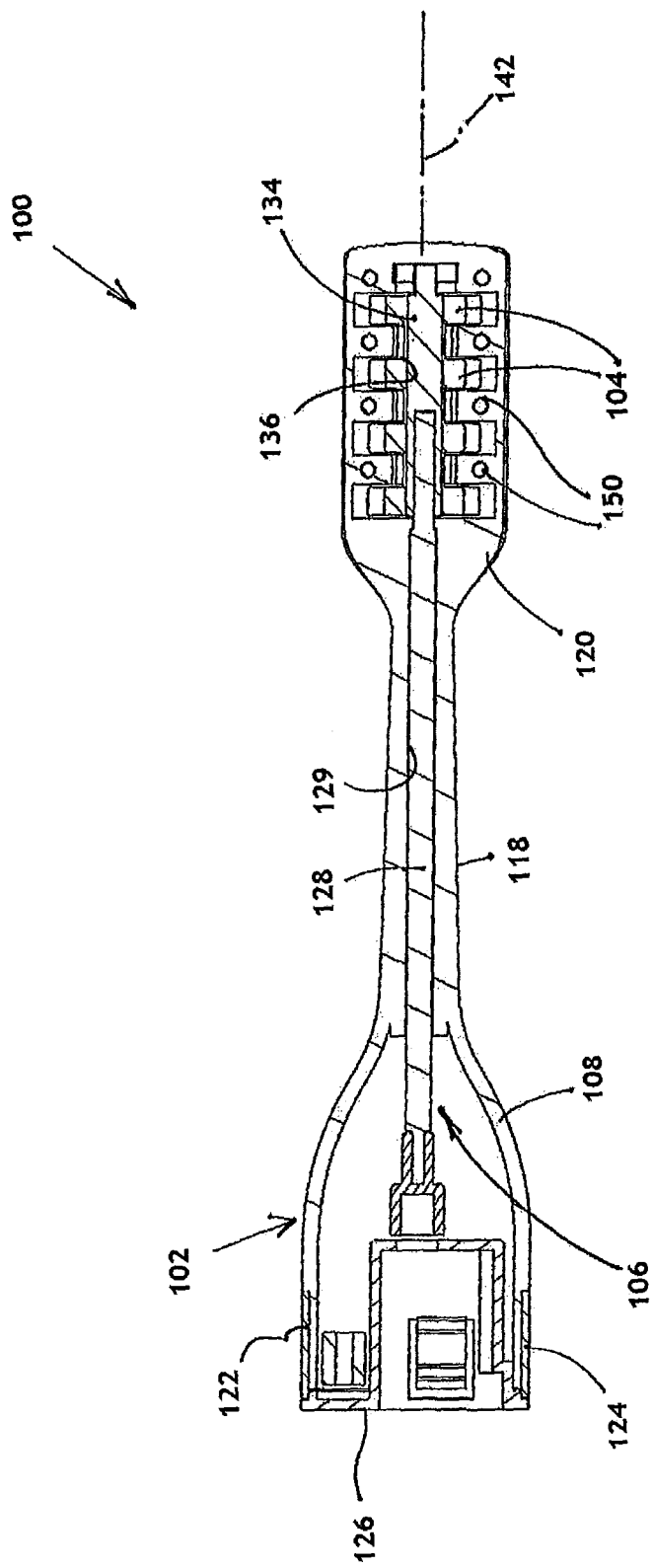
FIG. 2 is a longitudinal cross-sectional view taken along line II-II in FIG. 1.
Figure 3:
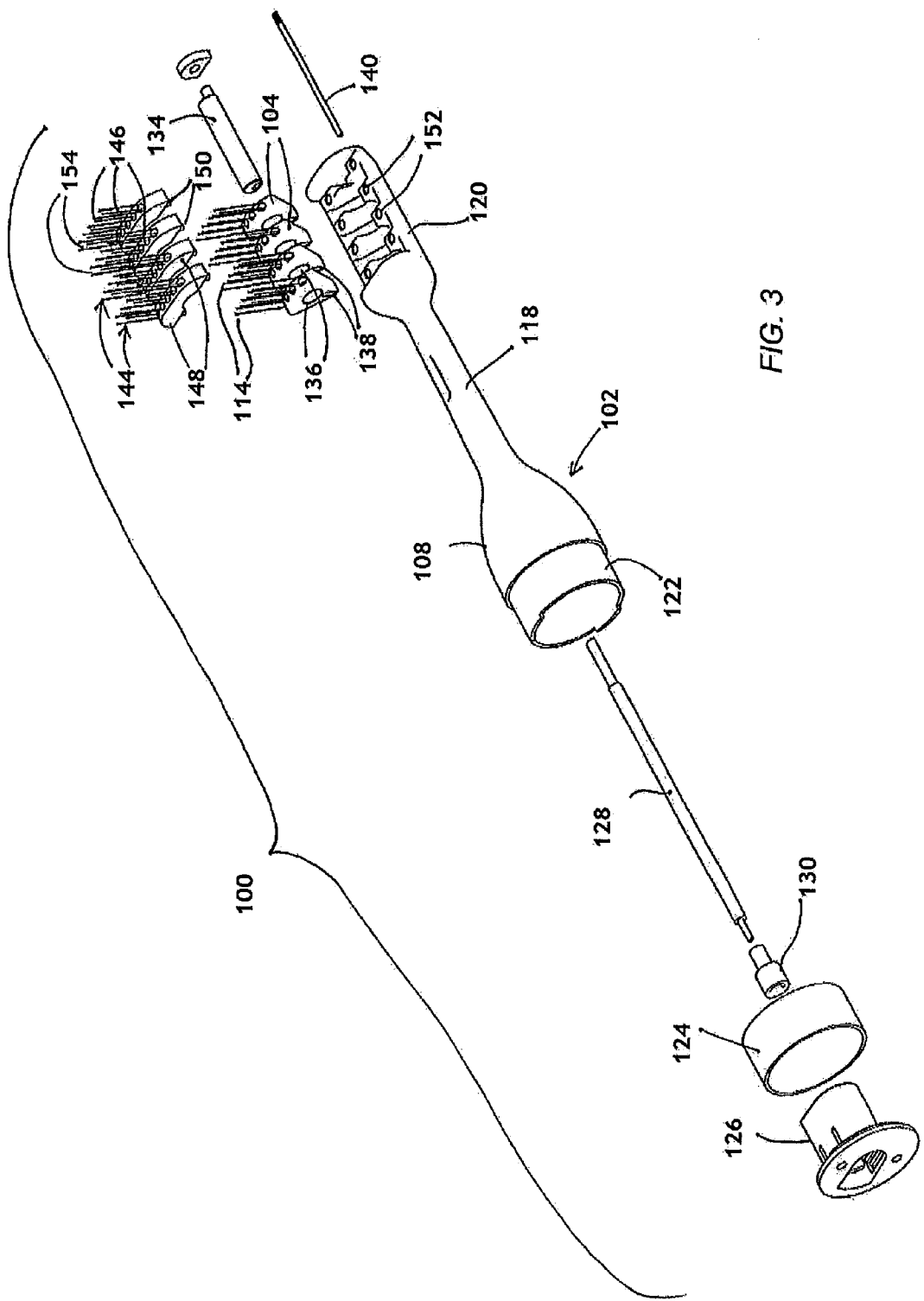
FIG. 3 is an exploded perspective view of the toothbrush module or assembly of FIGS. 1 and 2.

FIGS. 1-3 depict an electric toothbrush module 100 that includes a frame assembly 102, a plurality of bristle holders 104 movably mounted to a distal end of the frame assembly, and a power transmission assembly 106. Frame 102 includes a base portion 108 that is removably connectable to a handle 110 containing an electric motor or drive 112. Power transmission assembly 106 is operatively connectable at an input or proximal end to electric motor or drive 112 upon attachment of frame base 108 to handle 110. Power transmission assembly 106 is and operatively connected at a downstream or distal end to bristle holders 104 so as to move bristle tips 114 on the bristle holder along an oval path 116 (see, e.g., FIG. 7) relative to frame 102. In a single cycle of movement along oval path 116, the bristles shift away from frame 102 and towards a user's teeth TT (arrows 116a), then along and in contact with the teeth TT in a direction away from the gum line (arrows 116b), then back towards the frame 102 and away from the teeth TT (arrows 116c), and subsequently along the frame 102 and out of contact with the teeth TT (arrows 116d).

As further depicted in FIGS. 1-3, frame 102 includes a hollow shank 118 continuous at a proximal end with base 108 and supporting at a free end a brush head housing or bracket 120. Base portion 108 is formed with a recessed shoulder 122 that is received in an annular sleeve 124. Sleeve 124 also receives, on a proximal side, a mounting bracket 126.

Power transmission assembly 106 comprises a drive shaft 128 rotatably disposed inside a channel or lumen 129 of frame shank 118 and fixed at a proximal end to a coupling element 130 that is releasably connectable to a rotor shaft 132 of electric motor or drive 112. At a distal end drive shaft 128 is inserted into, and is rotationally rigid with, a camming shaft 134. Camming shaft 134 may be fixed to drive shaft 128 by epoxy or other adhesive. Camming shaft 134, which is a part of power transmission assembly 106, traverses openings or apertures 136 in respective bristle holders 104. Camming shaft 134 is in contact with surfaces (not separately designated) of bristle holders 104 that define apertures 136. Camming shaft 134 is eccentrically mounted relative to drive shaft 128 and, during rotation thereof, negotiates an oval path which is transmitted to bristle holders 104, so that bristle tips 114 move along oval path 116. Bristle holders 104 therefore function as camming-action receiver elements which receive the eccentric motion of camming shaft 134 and, in response thereto, generate the oval-path motion of bristle tips 114.

Bristle holders or camming-action receivers 104 are additionally formed with respective elongate slots 138 which are traversed by a pin 140 that is fixed to brush head 120. Pin 140 extends longitudinally along brush head 120, in parallel to a rotation axis 142 of drive shaft 128 and camming shaft 134. Slots 138 and pin 140 cooperate to permit limited rotational and translational movement of bristle holders 104, necessary for movement of bristle tips 114 along oval path 116.

Bristle holders 104 are spaced longitudinally along the axis of frame 102, which axis generally coincides with drive shaft rotation axis 142. Camming shaft 134 is disposed partially inside the aperture 136 of each bristle holder or receiver element 104 so as to roll in contact with a surface of each aperture. As depicted in FIGS. 1-3, bristle holders 104 are independent elements but execute a parallel motion in tandem, with the bristle tips 114 all moving along the same oval path, owing to the common linkage to the camming shaft 134. Alternatively, the bristle holders may be fixed to one another, collectively serving as a unitary camming-action receiver element.

Brush head 120 also carries four auxiliary bristle arrays 144 each comprising a plurality of bristle tufts 146 mounted in linear alignment via glue, heat welding, or anchor plates or loops to a common support 148. Bristle arrays 144 are stationary relative to frame 102. Each support 148 is fixed to brush head 120 by a pair of pegs 150 force fit (and optionally glued or ultrasonically welded) into respective holes 152 in the brush head. Bristle tufts 146 assist a user in positioning the toothbrush module 100 relative to target teeth. To that end bristle tufts 146 have lengths such that free ends 154 of the bristle tufts are approximately coplanar with moving bristle tips 114 at a maximum extension of bristle holders 104 away from frame assembly 102 and particularly brush head 120.

Toothbrush module 100 further comprises an orientation sensor 156 (FIG. 18) mounted to frame 102 (in handle 110 or base portion 108) and adapted to detect an orientation of the frame. Orientation sensor 156 is operatively connectable to electric motor or drive 112 and/or operatively or connected to power transmission assembly 106 for controlling a direction of motion of bristle holders 104 so that bristle tips 114 trace oval path 116 in a direction depending on orientation of frame 102.

Sensor 156 is configured to detect at least two alternative orientations of frame 102 and to induce or enable a motion of bristle holder 104 in one direction along path 116 when toothbrush module 100 is in a first of the alternative orientations and in an opposite direction when the toothbrush module is in a second of the alternative orientations. In brief, orientation sensor 156 functions to detect the direction that toothbrush module 100 and the bristles thereof are facing and concomitantly the side of brush head 120 on which the target tooth surface TT lies.

Sensor 156 may take the form of a ball sensor as discussed in detail below with reference to FIGS. 16A-16D. Alternatively, sensor 156 includes a gravity switch or accelerometer as discussed below with reference to FIGS. 17A-17D.

Figure 4:
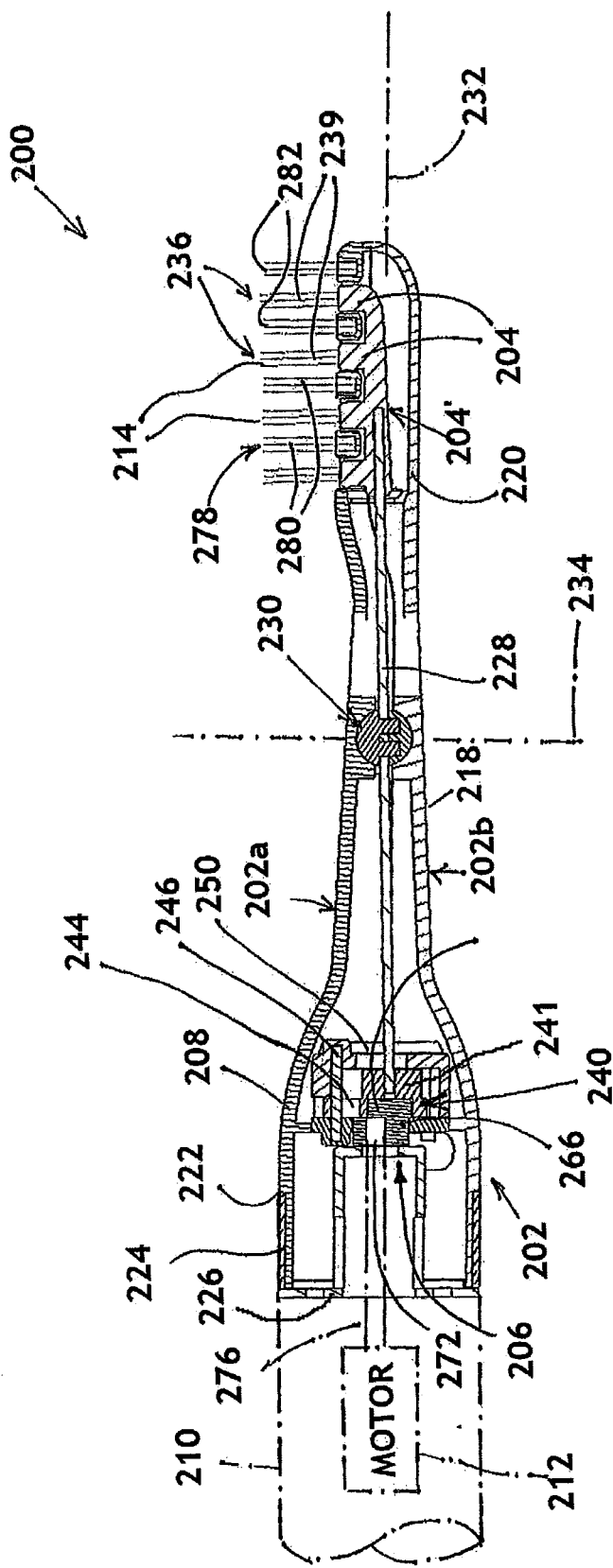
FIG. 4 is a longitudinal cross-sectional view of another electric toothbrush module or assembly in accordance with the present invention.
Figure 5:
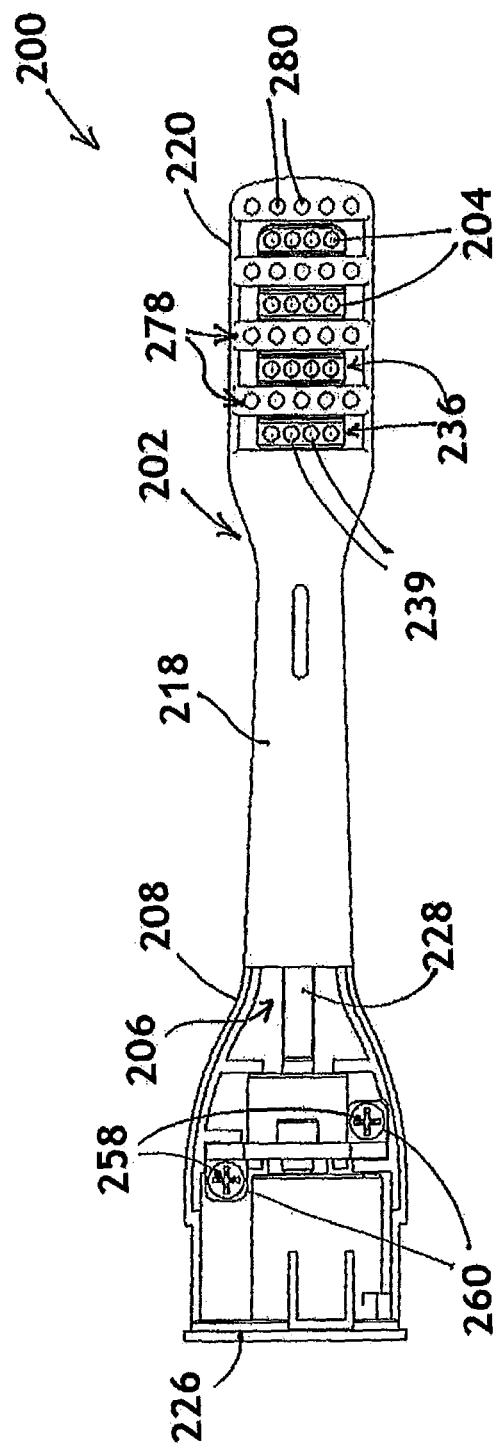
FIG. 5 is a elevational view taken from the top in FIG. 4, with a base portion of a frame or shell partially removed.
Figure 6:
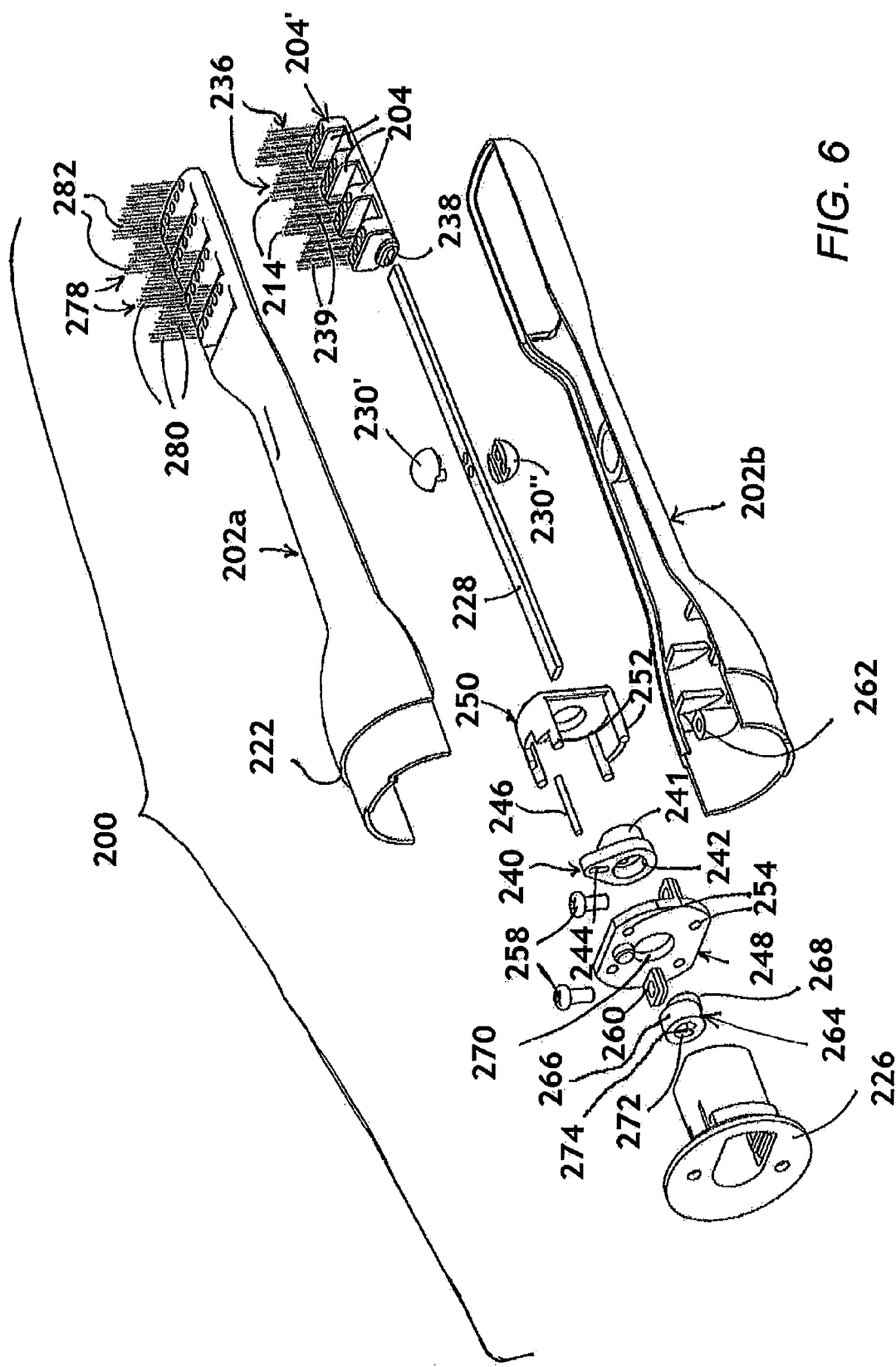
FIG. 6 is an exploded perspective view of the toothbrush module or assembly of FIGS. 4 and 5.

FIGS. 4-6 depict another electric toothbrush module 200. Module 200 includes a frame assembly 202, a plurality of bristle holders 204 movably mounted to a distal end of the frame assembly, and a power transmission assembly 206. Frame 202 comprises two longitudinal frame shells or halves 202a and 202b. When assembled, frame 202 includes a base portion 208 that is removably connectable to a handle 210 containing an electric motor or drive 212. Base portion 208 is formed with a recessed shoulder 222 that is received in an annular sleeve 224. Sleeve 224 also receives, from a proximal side, a mounting bracket 226. Assembly frame 202 further includes a hollow shank 218 and a hollow head or housing 220.

Power transmission assembly 206 is operatively connectable at an input or proximal end to electric motor or drive 212 upon attachment of frame base 208 to handle 210. Power transmission assembly 206 is operatively connected at a downstream or distal end to bristle holders 204 so as to move bristle tips 214 along an oval path 216 (see, e.g., FIG. 15) relative to frame 202. In a single cycle of movement along oval path 216, the bristles shift away from frame 202 and towards a user's teeth TT (arrows 216a), then along and in contact with the teeth TT in a direction away from the gum line (arrows 216b), then back towards the frame 202 and away from the teeth TT (arrows 216c), and subsequently along the frame 202 and out of contact with the teeth TT (arrows 216d).

Power transmission assembly 206 essentially comprises a flattened bar or rod 228, exemplarily made of steel, that extends through frame shank 218. A pair of ball halves 230' and 230" are attached to rod 228 and form a pivot ball 230 that is rotatably housed in shank 218. Ball 230 serves as a universal joint allowing rod 228 to swivel about a longitudinal axis 232 of shank 218 (and frame 202), as well as pivot about a transverse axis 234. Ball 230 is typically positioned at about the geometric center of rod 228. However, the exact position may be varied to adjust the size of the oval path 216 negotiated by bristle tips 214.

Bristle holders 204, which support respective linear arrays 236 of bristle tufts 239, are rigidly connected in parallel to one another as parts of a composite bristle unit 204' disposed in brush head housing 220. At a distal end, rod 228 is inserted into a flattened channel 238 in bristle unit 204' and is rigidly secured to the bristle unit 204'. At a proximal end, rod 228 is coupled to a camming-action receiver element 240 and is particularly inserted into a slotted protuberance 241 thereon. Receiver element 240 is formed with an aperture 242 defining a cylindrical camming surface (not separately designated) and is further formed with an elongate slot 244. Slot 244 is traversed by an anchor pin 246, stationary relative to frame 202 and secured at opposite ends to the frame via a pair of secondary brackets 248 and 250. Bracket 250 is provided at respective corners with four legs or pegs 252 that are inserted into respective holes 254 in bracket 248. A pair of bolts 258 are inserted through respective flanges 260 in bracket 248 and screwed into holes or sockets 262 in frame shell 202b.

Slot 244 and pin 246 cooperate to permit limited rotational and translational movement of receiver element 240, that limited movement giving rise to movement of bristle tips 214 along oval path 216.

Power transmission assembly 206 further comprises a power coupling element 264 that includes a cylindrical disk 266 and a camming element 268. Disk 266 is rotatably mounted in a circular opening 270 in bracket 248, while camming element 268 is inserted into aperture 242 of camming-action receiver element 240. Disk 266 is formed with a recess 272 and a keying ridge 274 therein for drivingly (and releasably) linking coupling element 264, and hence the entire power transmission assembly 206, to rotor shaft 276 of electric motor 212. Camming element 268 is eccentrically mounted to disk 266 and, upon coupling of the drive motor 210 to coupling element 266, so induces an oval movement of receiver element 240, which movement is transmitted by rod 228 to bristle unit 204' and accordingly to bristle tips 214. Camming element 268 is in contact with the surface (not separately designated) of camming-action receiver element 240 that surrounds and thus defines aperture 242.

Bristle holders 204 are spaced longitudinally along unit 204' and concomitantly along axis 232 of frame 202. While bristle holders 204 are fixed to one another, an alternative configuration contemplates that bristle holders 204 are independent elements executing a parallel motion in tandem, with the bristle tips 214 all moving along the same oval path, owing to a common linkage to drive rod 228.

Brush head 220 also carries four auxiliary bristle arrays 278 each comprising a plurality of bristle tufts 280 mounted in linear alignment to frame shell 202a at brush head 220. Bristle arrays 280 are thus stationary relative to frame 202. Bristle tufts 280 may be configured to assist a user in positioning the toothbrush module 200 relative to target teeth TT. To that end bristle tufts 280 may be provided with such lengths that free ends 282 of the bristle tufts are approximately coplanar with moving bristle tips 214 at a maximum extension of bristle holders 204 away from frame assembly 202 and particularly brush head 220. A user thus positions toothbrush module 200 so that bristle ends 282 engage the buccal, labial, lingual or palatal surfaces of one or more teeth. Depending on the orientation of the toothbrush, for instance, whether the user is brushing the lingual or the buccal surfaces of the teeth of the lower right jaw, the bristle holders 204 are driven toward one side of the brush head 220 or the other during the brushing stroke 216b of path 216.

As discussed above with reference to FIGS. 1-3, toothbrush module 200 further comprises an orientation sensor 156 (FIG. 18) mounted to frame 202 and adapted to detect an orientation of the frame. Orientation sensor 156 is operatively connectable to electric motor or drive 212 and/or operatively or connected to power transmission assembly 206 for controlling a direction of motion of bristle holders 204 so that bristle tips 214 trace oval path 216 in a direction depending on orientation of frame 202.

Sensor 156 is configured to detect at least two alternative orientations of frame 202 and to induce or enable a motion of bristle holder 204 in one direction along path 216 when toothbrush module 200 is in a first of the alternative orientations and in an opposite direction when the toothbrush module is in a second of the alternative orientations. In brief, orientation sensor 156 functions to detect the direction that toothbrush module 200 and the bristles thereof are facing and concomitantly the side of brush head 220 on which the target tooth surface TT lies.

Figure 7:
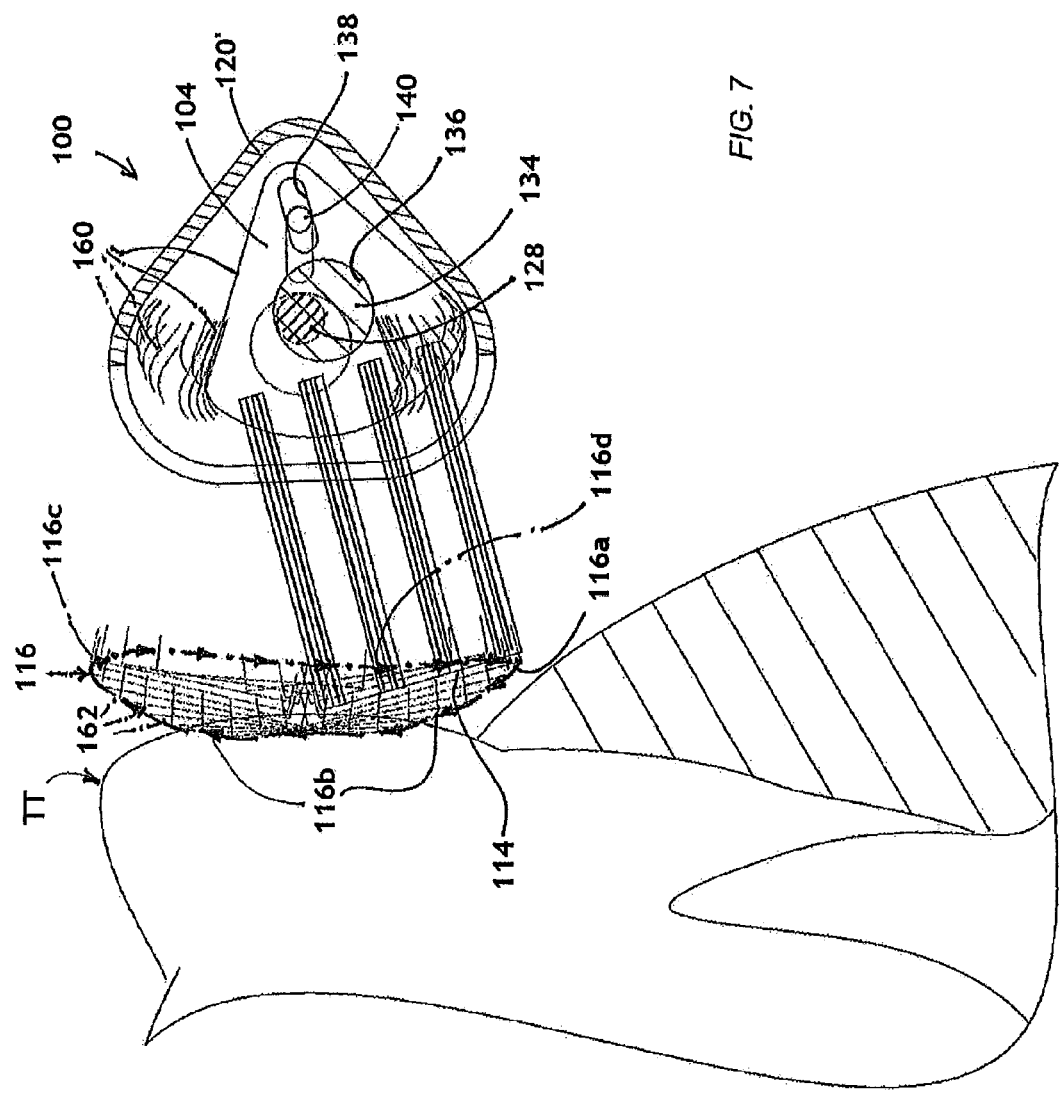
FIG. 7 is a schematic transverse cross-sectional view of a brush head of a toothbrush module in accordance with the present invention, diagrammatically depicting successive positions of a bristle holder and a path of motion of bristle tips.

FIG. 7 diagrammatically depicts the operation of toothbrush module 100 (with a triangularly shaped head 120'), showing multiple successive positions 160 of bristle holder 104 and multiple successive positions 162 of bristle tips 114. The direction of motion of bristle tips 114 along path 116 as indicated by arrows 116a, 116b, 1116c, 116d would be reversed if teeth TT were in an upper jaw rather than a lower jaw as depicted. This reversal in motion direction is implemented automatically by the circuit shown in FIG. 18, upon detection by sensor 156 of a change in brush orientation.

Figure 8:
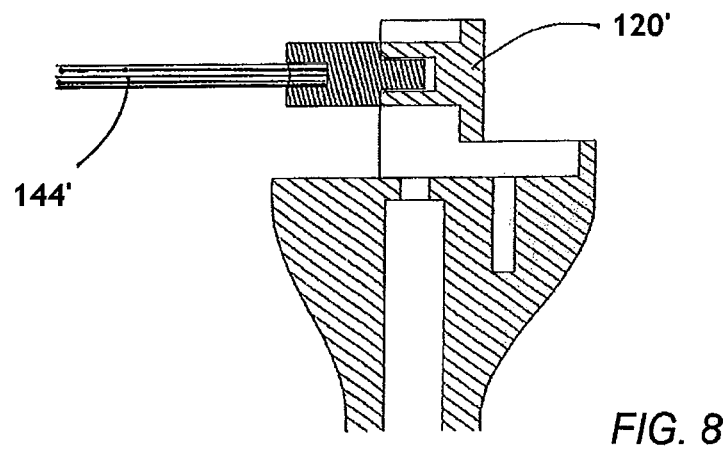
FIG. 8 is a partial longitudinal cross-sectional view of a brush head in accordance with the present invention, taken along line VIII-VIII in FIG. 9, showing stationary auxiliary bristles.
Figure 9:
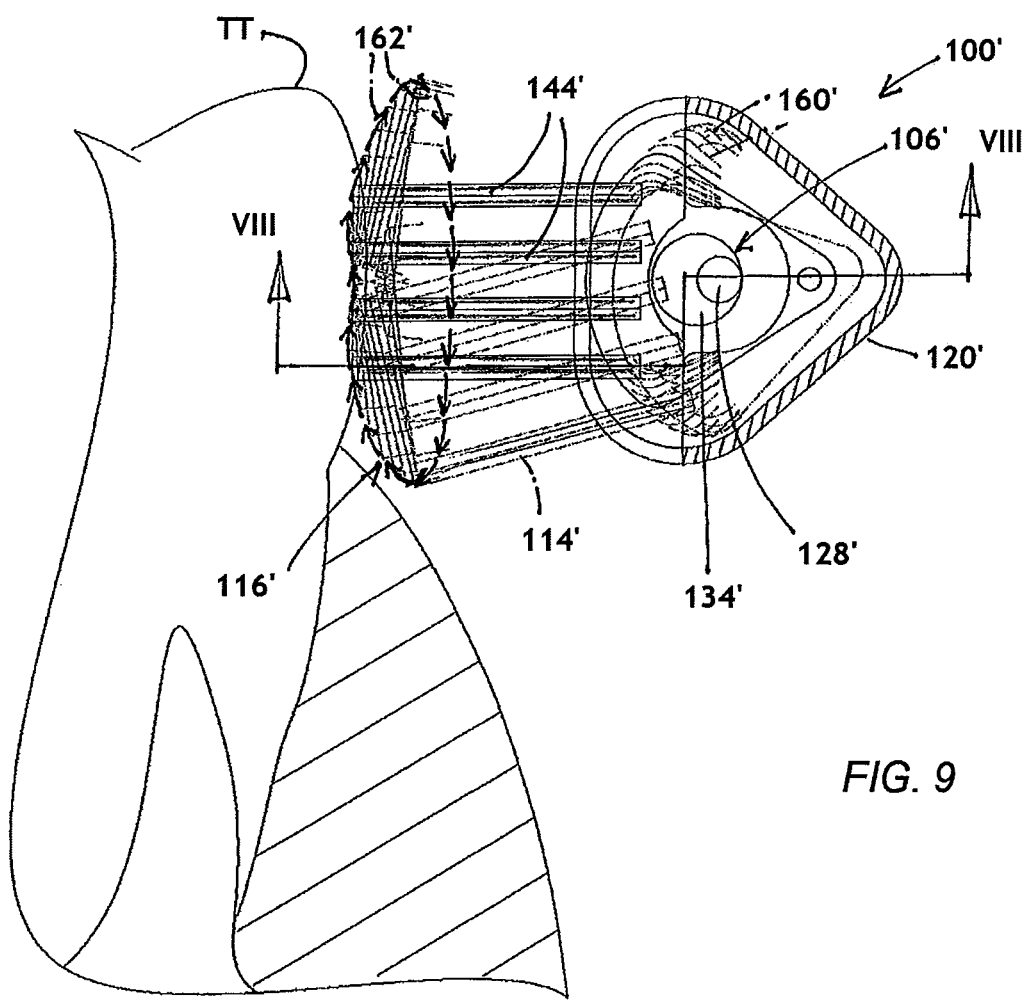
FIG. 9 is a schematic transverse cross-sectional view of the brush head of FIG. 8, diagrammatically depicting successive positions of a bristle holder and a path of motion of bristle tips.

FIG. 7 shows operative configurations of toothbrush module 100, without stationary bristle arrays 144. FIGS. 8 and 9 illustrate a modified toothbrush module 100' with a plurality of spaced auxiliary bristle tufts 144' mounted in stationary relationship to a brush head 120'. A bristle holder 104' carrying bristles 114' is movable along an oval path 116' by a power transmission train 106' including a drive shaft 128' and an eccentric cam shaft 134'. Bristle holder 104' traverses multiple successive positions 160' and tips of bristles 114' pass through multiple successive positions 162'.

Figure 10:
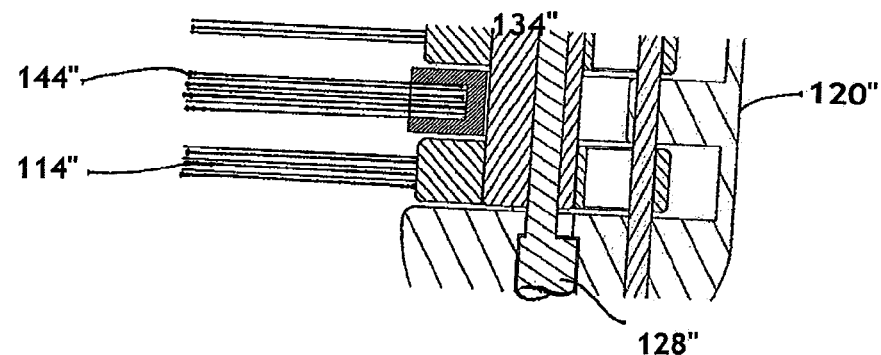
FIG. 10 is a partial longitudinal cross-sectional view of a head of another toothbrush module or assembly in accordance with the present invention, showing stationary auxiliary bristles and a movable bristle holder.
Figure 11:
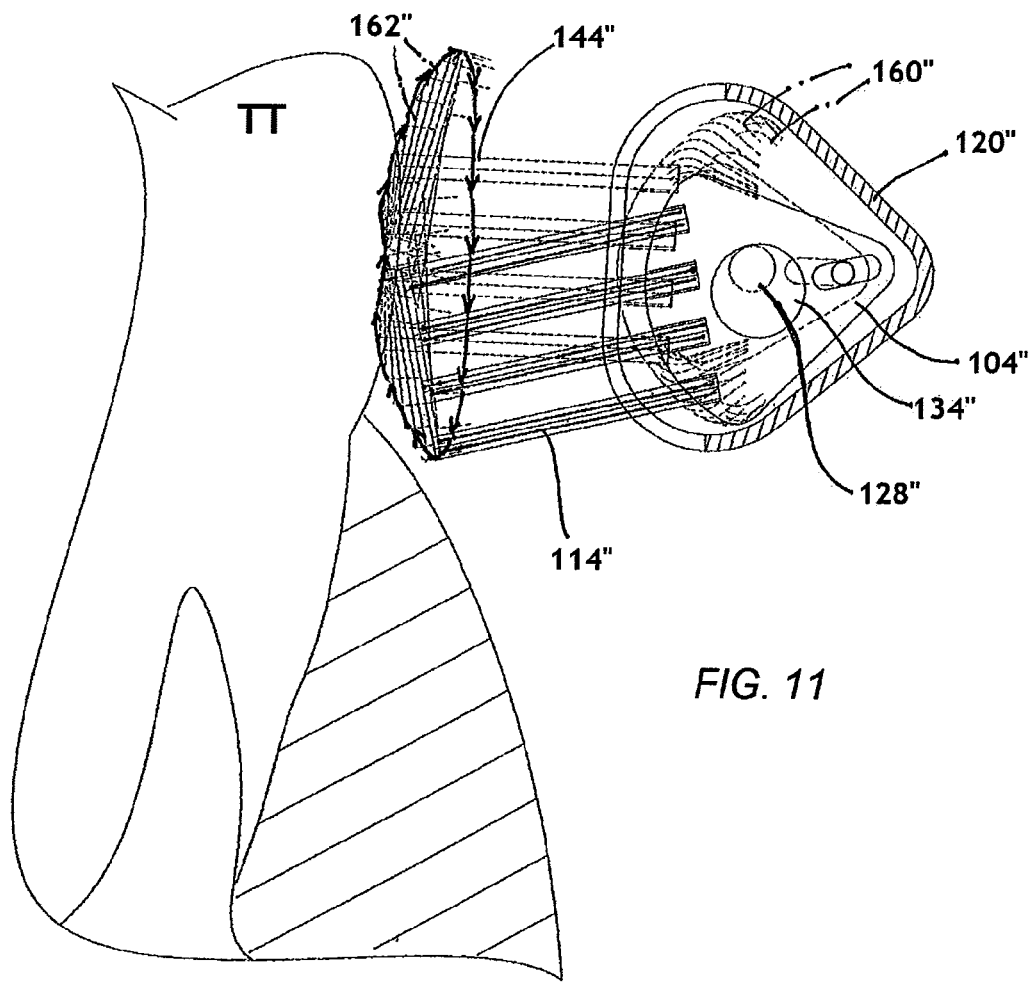
FIG. 11 is a schematic transverse cross-sectional view of the brush head of FIG. 10, diagrammatically depicting successive positions of a bristle holder and a path of motion of bristle tips.

FIGS. 10 and 11 illustrate a modified toothbrush module 100" with a plurality of linear bristle arrays 144" mounted in stationary relationship to a brush head 120". A bristle holder 104" carrying linear bristle arrays 114" is movable along an oval path 116" by a power transmission train 106" including a drive shaft 128" and an eccentric cam shaft 134". Bristle holder 104" traverses multiple successive positions 160" and tips of bristles 114" pass through multiple successive positions 162".

Figure 12:
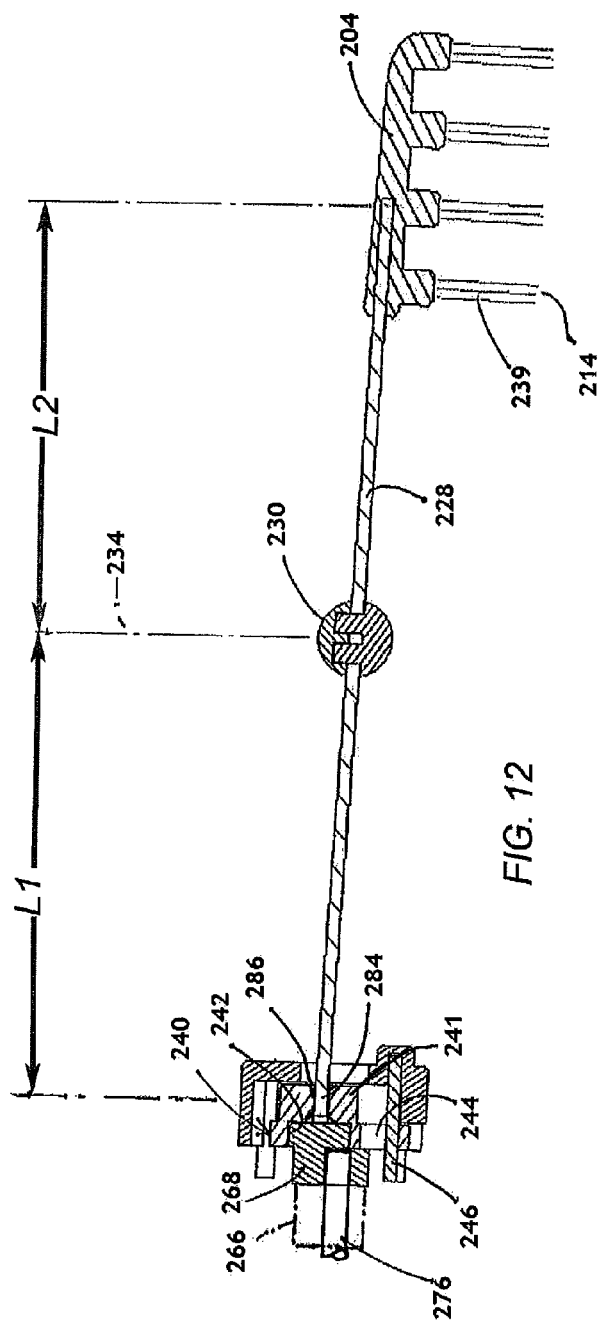
FIG. 12 is a schematic side elevational view of a power transmission assembly in the toothbrush module of FIGS. 4-6.
Figure 13:
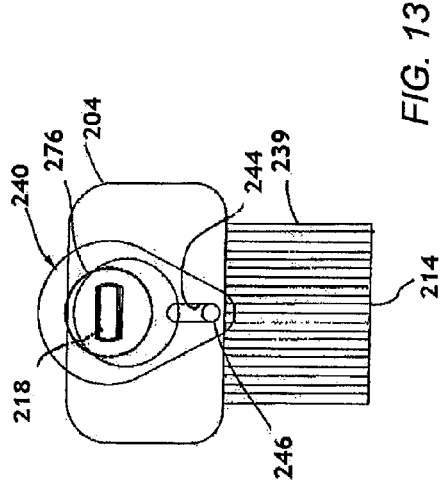
FIG. 13 is a schematic axial elevational view of selected components of the power transmission assembly of FIG. 12, together with a bristle holder of the toothbrush module.

FIGS. 12 and 13 provide simplified views showing key components of power transmission assembly or train 206 of the toothbrush embodiment of FIGS. 4-6. A proximal end 284 of rod 228 is disposed in a recess 286 in protrusion 241 of camming-action receiver element 240. Pivot ball 230 is located a distance L1 from recess 286 that is approximately equal to the distance L2 between pivot ball 230 and bristle holder unit 204'. As indicated above, adjusting the position of ball 230 along shank 218 and accordingly the relative distances L1 and L2 can be undertaken to magnify or diminish the proportional movement of bristle holders 204 relative to the movement of protrusion 241.

Figure 14:
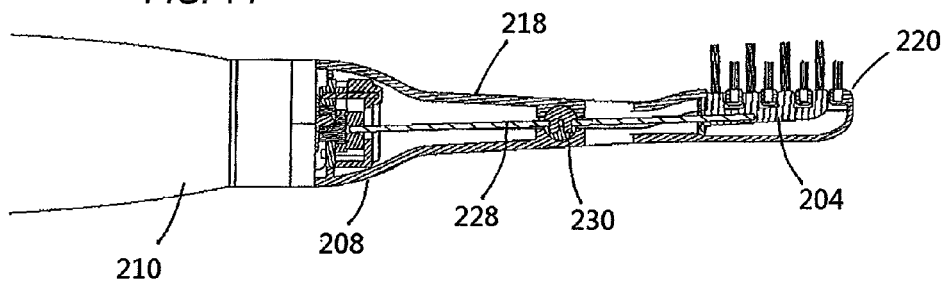
FIG. 14 is a schematic longitudinal cross-sectional view of the toothbrush module or attachment of FIGS. 4-6. showing selected power transmission thereof.

FIG. 14 is a simplified or diagrammatic view of toothbrush module 200, showing ball joint or pivot ball 230 at a position more proximate to head 220. The natural result is a reduction in the magnitude of movement along path 216.

Figure 15:
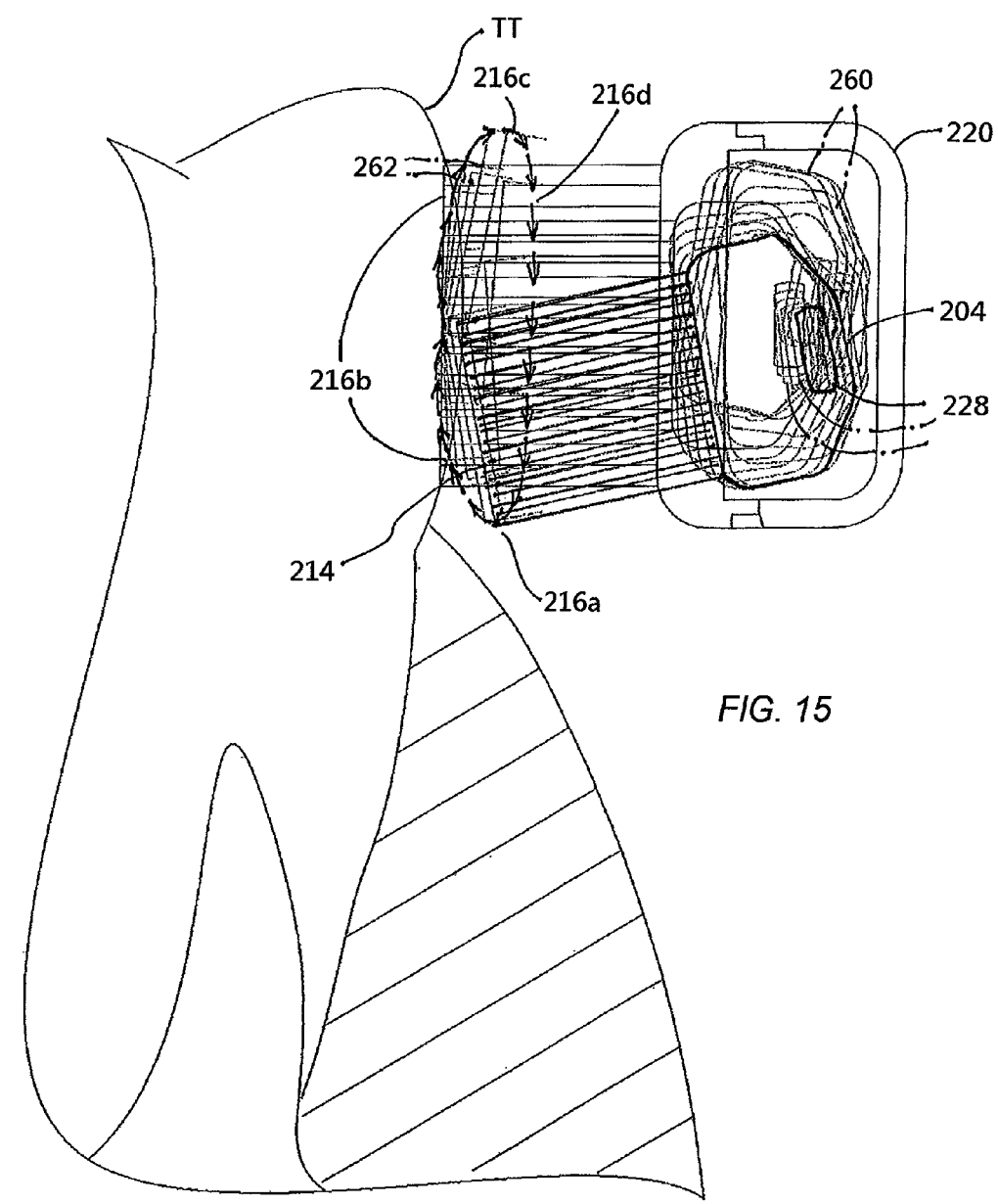
FIG. 15 is a schematic transverse cross-sectional view of a brush head of FIG. 14, diagrammatically depicting successive positions of a bristle holder and a path of motion of bristle tips.

FIG. 15 diagrammatically illustrates the operation of toothbrush module 200 (with head 220 of an oblong cross-section having a preferably minimized thickness TH), showing multiple successive positions 260 of a bristle holder 204 and multiple successive positions 262 of bristle tips 214. The direction of motion of bristle tips 214 along path 216 as indicated by arrows 216a, 216b, 216c, 216d would be reversed if teeth TT were in an upper jaw rather than a lower jaw as depicted. This reversal in motion direction is implemented automatically by the circuit shown in FIG. 18, upon detection by sensor 156 of a change in brush orientation.

FIGS. 16A-16D show four different orientations of a toothbrush module 100 or 200, schematically represented by an exaggeratedly oval handle 302, with an orientation sensor (156 in FIG. 18) in the form a ball sensor 304. Ball sensor 304 includes a square or cubical casing 306 and a freely rolling ball 308 and four electrodes or contact pins 310 therein, the pins being attached to a printed circuit board base panel 312 of the casing 306. Each electrode or contact pin 310 is located along a respective wall of casing 306, designated by respective lettering A, B, C, D. A generic brush or bristle array 312 indicates, by its location and orientation relative to handle 302, the location in the user's jaw of the teeth being brushed. Ball 308 and electrodes or contact pins 310 are made of, or coated with, a material of low electrical resistance such as nickel; thus ball 308 may be a nickel-plated steel ball and pins 310 nickel plated steel.

Figure 16A:
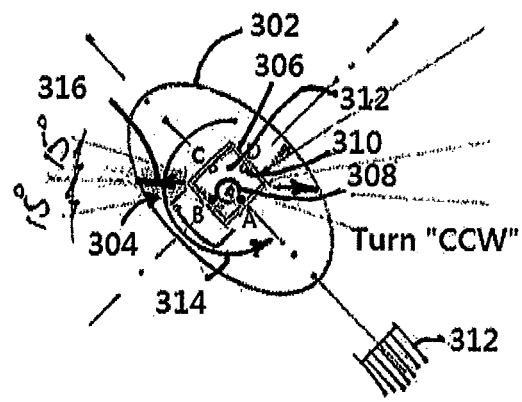
FIGS. 16A-16D are schematic representations of a ball sensor for detecting toothbrush orientation, showing four different orientations of a toothbrush.

FIG. 16A depicts a toothbrush orientation for cleaning the front lower outer tooth surfaces, the right lower inner tooth surfaces, and the left lower outer tooth surfaces. Ball 308 rests against and closes a circuit with pins 310 along walls A and B of casing 306.

Figure 16B:
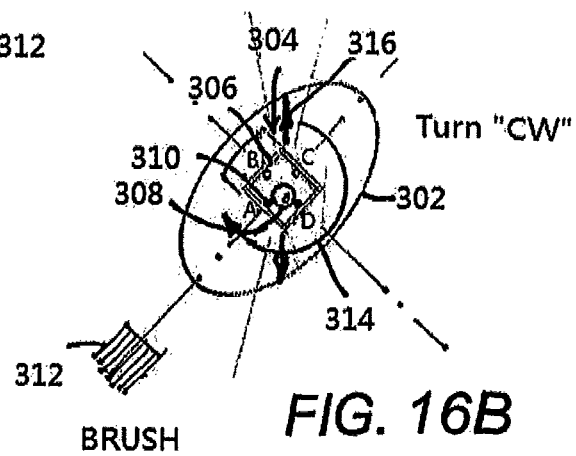

FIG. 16B depicts a toothbrush orientation for cleaning the front lower inner tooth surfaces, the right lower outer tooth surfaces, and the left lower inner tooth surfaces. Ball 308 rests against and closes a circuit with pins 310 along walls A and D of casing 306.

Figure 16C:
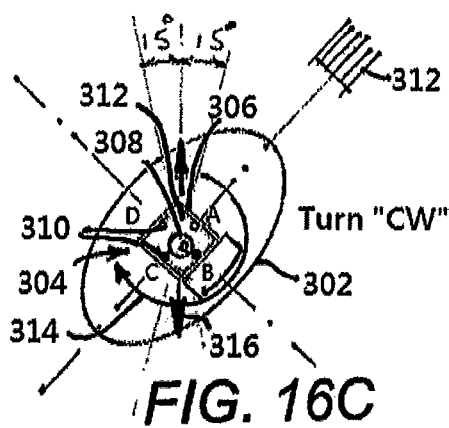

FIG. 16C depicts a toothbrush orientation for cleaning the front upper outer tooth surfaces, the left upper outer tooth surfaces, and the right upper inner tooth surfaces. Ball 308 rests against and closes a circuit with pins 310 along walls C and B of casing 306.

Figure 16D:
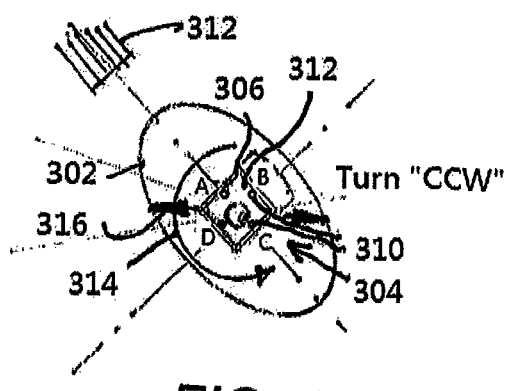

FIG. 16DC depicts a toothbrush orientation for cleaning the front upper inner tooth surfaces, the right upper outer tooth surfaces, and the left upper inner tooth surfaces. Ball 308 rests against and closes a circuit with pins 310 along walls C and D of casing 306.

A curved arrow 314 in FIGS. 16A-16D represents an angular direction for a tooth-contacting "power" stroke in each respective brush orientation. Oppositely pointing arrowheads 316 represent a sensor axis.

Pin 310 along wall C may be a negative or low voltage pole, while pin 310 along wall A is a positive or high voltage pole. The motor turns in one direction, say counterclockwise, if pin B is positive or pin D is negative, and in the opposite direction if pin B is negative or pin D is positive.

FIGS. 17A-17D show four different orientations of a toothbrush module 100 or 200, schematically represented by an exaggeratedly oval handle 402, with an orientation sensor (156 in FIG. 18) in the form a gravity sensor or accelerometer 404. Sensor 404 includes an eccentric mass 406 and conventional mechanical and electrical components (not shown)(e.g., piezoelectric crystals and detector circuit). A generic brush or bristle array 412 indicates, by its location and orientation relative to handle 402, the location in the user's jaw of the teeth being brushed.

Figure 17A:
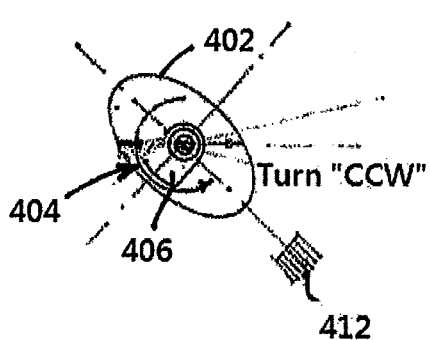
FIGS. 17A-17D are schematic representations of a gravity switch or sensor or detecting toothbrush orientation, showing four different orientations of a toothbrush.
Figure 17B:
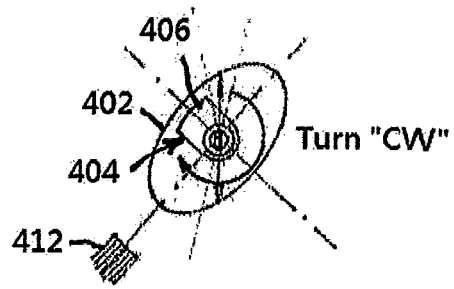
Figure 17C:
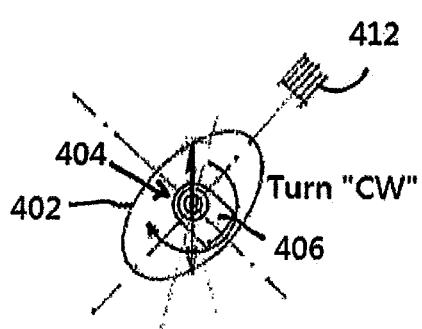
Figure 17D:
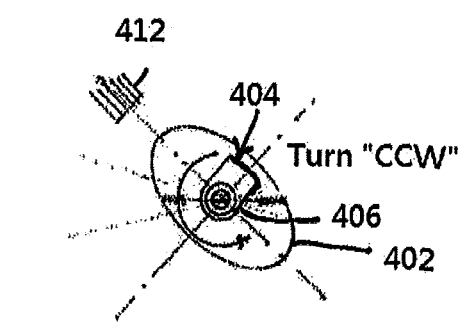

FIG. 17A depicts a toothbrush orientation for cleaning the front lower outer tooth surfaces, the right lower inner tooth surfaces, and the left lower outer tooth surfaces. FIG. 17B depicts a toothbrush orientation for cleaning the front lower inner tooth surfaces, the right lower outer tooth surfaces, and the left lower inner tooth surfaces. FIG. 16C depicts a toothbrush orientation for cleaning the front upper outer tooth surfaces, the left upper outer tooth surfaces, and the right upper inner tooth surfaces. FIG. 16DC depicts a toothbrush orientation for cleaning the front upper inner tooth surfaces, the right upper outer tooth surfaces, and the left upper inner tooth surfaces.

Figure 18:
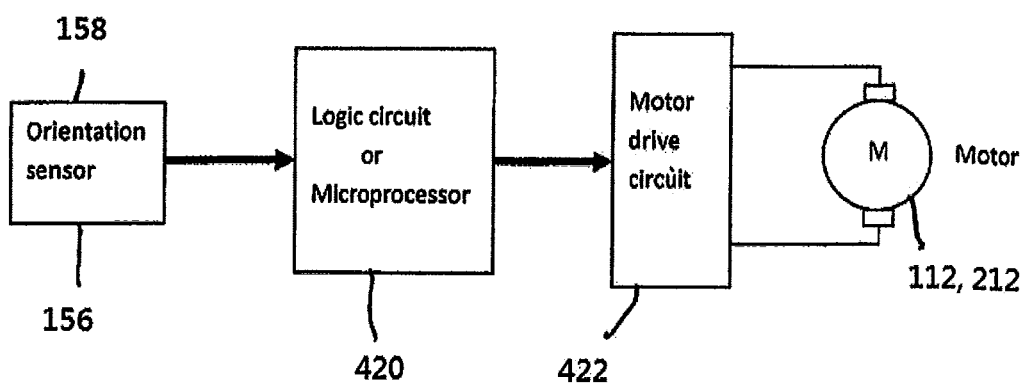
FIG. 18 is a block diagram of an electrical circuit including an orientation sensor for controlling brush direction movement in accordance with toothbrush orientation.

As shown in FIG. 18, a circuit for controlling the direction of movement of bristle holder(s) 104 or 204 includes orientation sensor 156 and a hard-wired logic circuit or a microprocessor 420, each configured for determining toothbrush orientation in accordance with signals from orientation sensor 156. The logic circuit or microprocessor 420 is connected to a motor drive circuit 422 in turn connected to the electric motor or drive 112, 212.

Toothbrush modules 100, 200 enable a user to brush teeth in a way to reduce the incidence of tooth decay, by reducing the likelihood of food particles being swept under the gums. The invention contemplates a method of automatically brushing the teeth wherein ones operates power transmission assembly 106 or 206, operatively connected to a bristle holder 104 or 204, so as to move bristle tips 114 or 214 on the bristle holder along an oval path 116 or 216 relative to toothbrush frame 102 or 202. In a single cycle of movement along the oval path 116 or 216, bristle tips 114 or 214 shift away from the frame 102 or 202 and towards the teeth TT, then along and in contact with the teeth in a direction away from the gum line, then back towards the frame 102 or 202 and away from the teeth TT, and subsequently along the frame 102 or 202 and out of contact with the teeth TT.

The method also contemplates an automatic control of the direction of movement of the bristle holder 104 or 204 so that the bristle tips 114 or 214 move in one direction or the opposite along the oval path 116 or 216, depending on brush orientation. The method may include operating orientation sensor 156 (304, 404) to detect two alternative orientations of the frame 102 or 402 and to induce or enable a motion of the bristle holder 104 or 204 in one direction when the toothbrush module 100 or 200 is in a first of the alternative orientations and in an opposite direction when the toothbrush is in a second of the alternative orientations.

The operating of power transmission assembly 106 or 206 may include moving camming element 134 or 268 along a circuit that is eccentric relative to a power transmission axis of rotor 132 or 276 and consequently moving camming-action receiver element 104 or 240.

It is to be noted that the oval paths 116 and 216 can be elongate or flattened, so that the approach strokes 116a, 216a and the retraction strokes 116c, 216c are small in comparison with the brushing strokes 116b, 216b and the return strokes 116d, 216d. Particularly with the provision of the stationary auxiliary bristle arrays 144 and 278, the motion of bristle ends 114 and 214 in a direction orthogonal to the tooth surfaces TT can be maintained exemplarily within a range of a few millimeters to about a centimeter.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A toothbrush module comprising:
a base connectable to a handle containing an electrically powered drive having a rotor;
an elongate hollow shaft or shank connected to said base, said shaft or shank defining a longitudinal axis at a distal end;
a brush head mounted to said shaft or shank at an end thereof opposite said base, said brush head including a bristle holder movable relative to said shaft or shank and said base; and
a power transmission assembly operatively connectable to the drive and operatively connected to said bristle holder, said power transmission assembly being configured to convert a rotary motion of said rotor into a motion of said bristle holder such that bristle tips thereof trace a generally oval path relative to said shaft or shank and said base, said oval path including a first path segment towards a tooth surface, a second path segment along said tooth surface and away from a respective gum line, a third path segment away from said tooth surface, and a fourth path segment in a direction opposite said second path segment and spaced away from the tooth surface,
said power transmission assembly including a camming element executing a motion that is eccentric relative to said axis, said camming element being fixed relative to said rotor,
said power transmission assembly further including a camming-action receiver element formed with an aperture, said camming element being disposed at least in part in said aperture in contact with a surface thereof, said receiver element having a slot traversed by a pin stationary relative to said base and said shaft or shank.

2. The toothbrush module defined in claim 1 wherein said bristle holder includes said receiver element.

3. The toothbrush module defined in claim 1 wherein said brush head includes a hollow housing disposed at an end of said shaft or shank opposite said base, said housing being stationary relative to said base, said bristle holder being disposed partially inside said housing.

4. A toothbrush module comprising:
a base connectable to a handle containing an electrically powered drive having a rotor;
an elongate hollow shaft or shank connected to said base, said shaft or shank defining a longitudinal axis at a distal end;
a brush head mounted to said shaft or shank at an end thereof opposite said base, said brush head including a bristle holder movable relative to said shaft or shank and said base;
a power transmission assembly operatively connectable to the drive and operatively connected to said bristle holder, said power transmission assembly being configured to convert a rotary motion of said rotor into a motion of said bristle holder such that bristle tips thereof trace a generally oval path relative to said shaft or shank and said base, said oval path including a first path segment towards a tooth surface, a second path segment along said tooth surface and away from a respective gum line, a third path segment away from said tooth surface, and a fourth path segment in a direction opposite said second path segment and spaced away from the tooth surface; and
an orientation sensor for detecting an orientation of the toothbrush module, said orientation sensor being operatively connected to at least one of said drive and said power transmission assembly for controlling a direction of motion of said bristle holder along said generally oval path in accordance with orientation of the toothbrush module, said orientation sensor taken from the group consisting of a ball sensor and a gravity switch.

5. The toothbrush module defined in claim 4 wherein said sensor is configured to detect at least two alternative orientations and to induce or enable a motion of said bristle holder in one direction along said oval path when the toothbrush module is in a first of said alternative orientations and in an opposite direction along said oval path when the toothbrush module is in a second of said alternative orientations.

6. A toothbrush module comprising:
a base connectable to a handle containing an electrically powered drive having a rotor;
an elongate hollow shaft or shank connected to said base, said shaft or shank defining a longitudinal axis at a distal end;
a brush head mounted to said shaft or shank at an end thereof opposite said base, said brush head including a bristle holder movable relative to said shaft or shank and said base:
a power transmission assembly operatively connectable to the drive and operatively connected to said bristle holder, said power transmission assembly being configured to convert a rotary motion of said rotor into a motion of said bristle holder such that bristle tips thereof trace a generally oval path relative to said shaft or shank and said base, said oval path including a first path segment towards a tooth surface, a second path segment along said tooth surface and away from a respective gum line, a third path segment from said tooth surface, and a fourth path segment in a direction opposite said second path segment and spaced away from the tooth surface; and
a camming element and a receiver element disposed proximate a proximal end of said shaft or shank, said power transmission assembly including a rod extending longitudinally through said shaft or shank, said rod being linked at a proximal end to said receiver element, said rod being connected at a distal end to said bristle holder, said rod being attached to a ball rotatably disposed in said shaft or shank between said base and said brush head.

7. A toothbrush module comprising:
a base connectable to a handle containing an electrically powered drive having a rotor;
an elongate hollow shaft or shank connected to said base, said shaft or shank defining a longitudinal axis at a distal end;
a brush head mounted to said shaft or shank at an end thereof opposite said base, said brush head including a bristle holder movable relative to said shaft or shank and said base;
a power transmission assembly operatively connectable to the drive and operatively connected to said bristle holder, said power transmission assembly being configured to convert a rotary motion of said rotor into a motion of said bristle holder such that bristle tips thereof trace a generally oval path relative to said shaft or shank and said base, said oval path including a first path segment towards a tooth surface, a second path segment along said tooth surface and away from a respective gum line, a third path segment away from said tooth surface, and a fourth path segment in a direction opposite said second path segment and spaced away from the tooth surface, wherein said bristle holder is one of a plurality of main bristle holders mutually interspaced in an axial or longitudinal direction along said brush head, each of said main bristle holders being formed with a respective aperture, said camming element being disposed partially inside each said aperture so as to roll in contact with a surface of each said aperture, said brush head including a plurality of auxiliary bristle holders that are stationary with respect to said shaft or shank and said base, said auxiliary bristle holders being disposed between respective ones of said main bristle holders and axially or longitudinally spaced from one another.

8. A toothbrush module comprising:

a frame assembly;

a bristle holder movably mounted to a distal end of said frame assembly; and a power transmission assembly operatively connectable to a drive motor and operatively connected to said bristle holder so as to move bristle tips on said bristle holder along an oval path relative to said frame, further comprising an orientation sensor mounted to said frame and adapted to detect an orientation of said frame, said orientation sensor being operatively connected to at least one of said drive motor and said power transmission assembly for controlling a direction of motion of said bristle holder so that said bristle tips trace said oval path in a direction depending on orientation of said frame, said power transmission assembly including a camming element executing a motion that is eccentric relative to a power transmission axis, said power transmission assembly further includes a caroming-action receiver element formed with an aperture, said caroming element being disposed at least in part in said aperture in contact with a surface thereof, said receiver element having a slot traversed by a pin stationary relative to said frame.

9. The toothbrush module defined in claim 8 wherein said sensor is configured to detect at least two alternative orientations of said frame and to induce or enable a motion of said bristle holder in one direction when the toothbrush module is in a first of said alternative orientations and in an opposite direction when the toothbrush module is in a second of said alternative orientations.

10. The toothbrush module defined in claim 9 wherein said sensor is taken from the group consisting of a ball sensor and a gravity switch or accelerometer.

11. The toothbrush module defined in claim 8 wherein said bristle holder includes said receiver element.

12. The toothbrush module defined in claim 8 wherein said camming element and said receiver element are disposed proximate a proximal end of said shaft or shank, said power transmission assembly including a rod extending longitudinally through said shaft or shank, said rod being linked at a proximal end to said receiver element, said rod being connected at a distal end to said bristle holder, said rod being attached to a ball rotatably disposed in said shaft or shank between said base and said brush head.

13. The toothbrush module defined in claim 8 wherein said bristle holder is one of a plurality of bristle holders mutually interspaced along a brush head at a distal end of said frame, each of said bristle holders being formed with a respective aperture, said camming element being disposed partially inside each said aperture so as to roll in contact with a surface of each said aperture.

14. The toothbrush module defined in claim 8 wherein said oval path includes components towards and away from said frame.

* * * * *